United States Patent [19]

Henry et al.

[11] Patent Number: 4,911,926

[45] Date of Patent: Mar. 27, 1990

[54] METHOD AND COMPOSITION FOR REDUCING POSTSURGICAL ADHESIONS

[75] Inventors: Raymond L. Henry, Grosse Pointe Woods, Mich.; Richard E. Leach, Rochester, Minn.

[73] Assignee: Mediventures Inc., Grosse Pointe Park, Mich.

[21] Appl. No.: 272,199

[22] Filed: Nov. 16, 1988

[51] Int. Cl.$^4$ .................. A61F 2/00; A01N 31/14; A61M 25/00; A61K 31/74

[52] U.S. Cl. .................................. 424/426; 424/78; 427/2; 427/4; 128/898; 514/723; 606/230

[58] Field of Search ............... 424/78, 426, 83; 427/2, 427/4; 514/723; 128/898, 334 R

[56] References Cited

U.S. PATENT DOCUMENTS

| | | | |
|---|---|---|---|
| 3,847,155 | 11/1974 | Bernaola | 424/78 |
| 4,043,344 | 8/1977 | Landi et al. | 128/335.5 |
| 4,047,533 | 9/1977 | Perciaccante et al. | 128/335.5 |
| 4,540,407 | 9/1985 | Dunn | 604/292 |
| 4,651,736 | 3/1987 | Sanders | 128/305 |

OTHER PUBLICATIONS

Surgery, Gynecology and Obstetrics, Sep., 1971, vol. 133, pp. 497–509 at pp. 502–503.
The Journal of Reproductive Medicine, Jan., 1987, pp. 17–20.
Journal of Surgical Research, vol. 14, No. 4, Apr., 1973, pp. 277–284.
British Journal of Surgery, 1964, vol. 51, No. 5, May.

Primary Examiner—C. Warren Ivy
Assistant Examiner—P. I. Curtis
Attorney, Agent, or Firm—Andrew E. Pierce

[57] ABSTRACT

A process and compositions for reducing post-surgical adhesion formation/reformation in mammals following surgical injury to the peritoneal or pleural cavity or organs situated therein. Both aqueous and non-aqueous compositions comprising a polyoxyalkylene block copolymer are applied to injured areas of the peritoneal or pleural cavity or organs situated therein subsequent to surgical injury.

10 Claims, No Drawings

METHOD AND COMPOSITION FOR REDUCING POSTSURGICAL ADHESIONS

BACKGROUND OF THE INVENTION

1. Field of the Invention

This invention relates generally to methods and compositions for reducing postsurgical adhesions in the abdominal or thoracic cavity of mammals.

2. Description of the Prior Art

There is a need for a method and composition suitable for use in preventing adhesion formation/reformation in mammals following surgical injury to the peritoneal or pleural cavity, or organs situated therein.

According to Ellis in a reviewed entitled "The Cause And Prevention Of Post-operative Intraperitoneal Adhesions" in *Surgery, Gynecology and Obstetrics* for September 1971, volume 133, pages 497-509, at pages 502-503, the prevention of adhesions has been the subject of an enormous amount of work since the beginning of this century. According to Ellis, these attempts have included means of preventing the fibrin-coated walls of the intestine from reaching each other by distending the abdomen with oxygen or filling the abdomen with saline solution, paraffin, olive oil, lanolin, concentrated dextrose solution, macromolecular solutions of all sorts, and silicones.

Caspi, Halperin, and Bukovsky in an article entitled "The Importance of Periadnexal Adhesions in Reconstructive Surgery for Infertility" appearing in *Fertility and Sterility* for March 1982, volume 31, number 3, pages 296-300, at page 299 indicate that despite experimental and clinical efforts in the prevention of adhesion formation following surgery, no major advances have thus far been achieved. The authors discuss the use of post-operative intraperitoneal installation of a mixture of hydrocortisone acetate, promethazine, and ampicillin. As an alternative method of treatment, a low molecular weight dextran (a glucocorticoid) was also instilled intraperitoneally in another group of patients. The authors conclude that the intraperitoneal installation of high doses of glucocorticoids combined with early hydrotubations seems to be a worthwhile method.

Musich and Behrman in an article entitled "Infertility Laparoscopy In Perspective: Review of 500 Cases" appearing in *The American Journal of Obstetrics and Gynecology* for June 1, 1982, pages 293-303, at page 300 in the discussion section of the article disclose that there is a need to prevent adhesions subsequent to surgery in view of a study of 35 patients which indicated that 30 of these patients having serious tuboplasties had severe adhesions, one-third of which were judged to be inoperable.

High molecular weight dextran either alone or in combination with dextrose has been used in the prevention of peritoneal adhesions subsequent to surgery. Dextran is clinically standardized to a low molecular weight of about 75,000 by partial hydrolysis and fractional precipitation of the high molecular weight particles which normally have molecular weights of up to 200,000. Dextran is a polymer of glucose which has a chain-like structure and is produced from sucrose by Leuconostoc bacteria. In articles appearing in *Fertility and Sterility*, volume 33, number, 6, June 1980, pages 660-662, Holtz, Baker, and Tsai and volume 34, number 4, October 1980, pages 394-395, by Holtz and Baker, results are reported of the adhesion reducing effects of a 32% (aqueous) solution of dextran 70 containing 10% dextrose (sold under the trade name HYSKON by Pharmacia, of Piscataway, N.J.). Holtz et al. postulate several mechanisms of action in the prevention of peritoneal adhesions utilizing HYSKON including a simple mechanical separation of adjacent surfaces, termed a hydroflotation effect.

Project coordinator diZerega and several contributors have reported the results of a large study in an article entitled "Reduction of Post-operative Pelvic Adhesions with Intraperitoneal 32% Dextran 70: A Prospective, Randomized Clinical Trial" in *Fertility and Sterility*, volume 40, number 5, for November 1983, pages 612-619. The authors, at page 618, indicate that the use of Dextran intraperitoneally has limitations such as the reported tendency of HYSKON to support bacterial proliferation and concern over the anaphylactoid potential of dextran. In addition, the benefit of Dextran 70 in preventing post-operative adhesions was shown to be limited to the more dependent regions of the pelvis.

Borten and Taymor in *Obstetrics and Gynecology*, volume 61, number 6, June 1983, pages 755-757 report in an article entitled "Recurrent Anaphylactic Reaction to Intraperitoneal Dextran 75 Used for Prevention of Postsurgical Adhesions". These authors indicate that anaphylactic reaction to Dextran administered intravenously is well documented and report such a reaction after intraperitoneal administration of Dextran.

Linsky in *The Journal of Reproductive Medicine* for January 1987, pages 17-20 in an article entitled "Adhesion Reduction in the Rabbit Uterine Horn Model Using an Absorbable Barrier, TC-7". These authors report that the use of a resorbable fabric barrier provides a significant reduction in post-operative adhesion formation and that no gross remnants of the fabric barrier material were noted, subsequent to initial placement, after a two week period.

Oelsner et al. in *The Journal of Reproductive Medicine* for November 1987, volume 32, number 11, pages 812-814, reported results of a comparison of sodium carboxylmethyl cellulose, 32% dextran 70, and condroitin sulfate to prevent the formation of postoperative adhesions in the rabbit uterus. The authors report superior results with condroitin sulfate which is described as a member of a family of biochemical compounds referred to as glycosaminoglycans (formerly termed mucopolysaccharides), to which hyaluronic acid, heparine sulfate and heparin also belong.

The use of ethylene oxide/propylene oxide block copolymers as surfactants for use in surgical scrub solutions and the topical application of 10% solutions of these copolymers to wounds is described in Edlich et al in the *Journal of Surgical Research*, volume 14, number 4, April 1973, pages 277-284. The test results indicate that the copolymers having an ethylene oxide:propylene oxide ratio of 4:1 provide less inflammatory response in a wound to which the copolymer is applied in comparison with a copolymer having an ethylene oxide:propylene oxide ratio of 1:4. There is no indication in Edlich et al or any prior art that such copolymers are useful in reducing post-operative adhesions.

SUMMARY OF THE INVENTION

Compositions and a process are disclosed for reducing post-surgical adhesion formation/reformation in mammals following surgical injury to the organs of the peritoneal or pleural cavity. Both aqueous and non-aqueous compositions comprising a polyoxyalkylene block copolymer are useful. Non-aqueous compositions can include a physiologically acceptable carrier liquid or can include a low molecular weight polyoxyalkylene block copolymer, having a molecular weight of less than 5000, in combination with a high molecular weight polyoxyalkylene block copolymer. The concentration of the block copolymer can be adjusted in the useful compositions of the invention to take advantage of gelation properties of certain polyoxyalkylene block copolymers. For instance, certain concentrations of aqueous solutions of certain of said block copolymers form clear gels at mammalian body temperatures but are liquids at ambient temperatures. Subsequent to deposition of the compositions of the invention in the peritoneal or pleural cavity of a mammal, the polyoxyalkylene block copolymer is absorbed by the tissues with which it is in contact and the block copolymer is eventually excreted in a non-metabolized form, mainly in the urine.

In addition to functioning as a means of reducing post-operative adhesion formation/reformation in mammals following surgical injury to the peritoneal or pleural cavity or organs situated therein, the polyoxyalkylene block copolymer is believed to provide an environment surrounding the surgical injury which accelerates the regrowth rate of the injured tissue. For instance, the polyoxyalkylene block copolymer can be instilled within the uterine cavity as a distending medium during diagnostic or operative intrauterine endoscopic procedures. This application has two advantages. First, since certain aqueous concentrations of the preferred polymers form a clear gel, their use is well suited for visualization of the uterine cavity. Second, since these aqueous solutions form a clear gel at body temperature, the use of said solutions to separate the uterine cavity walls will diminish or prevent post-surgical adhesion formation.

Optionally, the polyoxyalkylene block copolymer can be utilized advantageously in combination with bacteriostatic or bactericidal agents, fibrinolytic agents, and agents effective in preventing leucocyte migration into the area of surgical injury.

DETAILED DESCRIPTION OF THE INVENTION

A process and compositions are disclosed for reducing post-operative adhesion formation/reformation in mammals following surgical injury to the peritoneal or pleural cavity or organs situated therein. In this specification and claims, the terms "peritoneal" and "abdominal" cavity are used as synonyms, as are the terms "pleural" and "thoracic" cavity. Both aqueous and non-aqueous compositions comprising at least one polyoxyalkylene block copolymer are useful in the process of the invention. The compositions can include at least one of a bacteriostatic or bactericidal agent, an agent effective in preventing leucocyte migration into the area of surgical injury, and a fibrinolytic agent.

The preferred aqueous compositons are prepared at concentrations so as to take advantage of the gelation properties of certain of said block copolymers. When certain of the polyoxyalkylene block copolymers of the invention are present in aqueous solutions at concentrations preferably of about 15% to about 30% by weight, such compositions can provide liquid compositions at ambient temperatures or below which revert to gel compositions upon contact with living mammalian tissue.

Alternatively, useful compositions of the invention include aqueous compositions comprising at least one polyoxyalkylene block copolymer which does not form gels as well as non-aqueous compositions comprising at least one polyoxyalkylene block copolymer in combination with a physiologically acceptable non-aqueous carrier liquid. It is believed that both the non-aqueous compositions of the invention and the aqueous compositions of the invention which do not form gels upon contact with living mammalian tissue function to prevent the formation/reformation of adhesions subsequent to surgical injury by a mechanism of action which has been termed in the prior art "hydroflotation".

Thus the injured tissues are prevented from contacting adjacent tissues by the means of the inclusion of a foreign fluid in the peritoneal or pleural cavity. With respect to those aqueous compositions of the invention which are chosen from polyoxyalkylene block copolymers of the invention which when prepared at suitable concentrations form gels upon contact with living mammalian tissue, it is believed that the mechanism of action to prevent the formation/reformation of adhesions is, in addition to hydroflotation, properly characterized as the result of separating the adjacent mammalian tissues by a firm, adherent gel coating.

The polyoxyalkylene block copolymer compositions of the invention include at least one block copolymer as below defined, optionally in combination with at least one of an adjuvant such as a humectant, a bactericide, a bacteriostatic agent, an agent to prevent leucocyte migration into the area of surgical injury, and a fibrinolytic agent. The copolymer is applied to injured tissue in a major amount in combination with a minor amount of said adjuvant. Useful humectants include, but are not limited to glycerin, propylene glycol, and sorbitol. Useful bactericides which can be administered in admixture with the aqueous or non-aqueous compositions of the invention include antibacterial substances such as B-lactam antibiotics, such as cefoxitin, n-formamidoyl thienamycin and other thienamycin derivatives, tetracyclines, chloramphenicol, neomycin, gramicidin, bacitracin, sulfonamides; aminoglycoside antibiotics such as gentamycin, kanamycin, amikacin, sisomicin and tobramycin; nalidixic acids and analogs such as norfloxacin and the antimicrobial combination of fludalanine/pentizidone; nitrofurazones, and the like. Antihistaminics and decongestants such as pyrilamine, cholpheniramine, tetrahydrazoline, antazoline, and the like, can also be used in admixtures as well as anti-inflammatories such as cortisone, hydrocortisone, beta-methasone, dexamethasone, fluocortolone, prednisolone, triamcinolone, indomethacin, sulindac, its salts and its corresponding sulfide, and the like.

Useful leucocyte migration preventing agents which can be used in admixtures include but are not limited to silver sulfadiazine, acetylsalicylic acid, indomethacin, and Nafazatrom. Useful fibrinolytic agents include urokinase, streptokinase, tissue plasminogen activator (TPA), and acylated plasmin. The block copolymer compositions of the invention comprise:

at least one polyoxyalkylene block copolymer of the formula $$Y[(A)_n\text{—}E\text{—}H]_x \qquad (I)$$

wherein A is a polyoxyalkylene moiety having an oxygen/carbon atom ratio of less than 0.5, x is at least 2, Y is derived from water or an organic compound containing x reactive hydrogen atoms, E is a polyoxyalkylene moiety constituting at least 60% by weight of the copolymer, n has a value such that the average molecular weight of A is at least about 500 to about 900, as determined by the hydroxyl number of a hydrophobe base intermediate, $$Y[(A)_n-H]_x \qquad (II)$$

and the total average molecular weight of the copolymer is at least 5000.

Post-operative pelvic adhesions have been associated with infertility. Significant periadnexal adhesions have been found, as reported by Musich and Behrman, as previously cited, upon laparoscopy in 72% of 106 patients having unexplained infertility who had previously undergone various pelvis surgical procedures. Prevention of such adhesions has been proposed in the prior art by treatment with aqueous dextran solutions of low molecular weight. The prior art use of aqueous dextran solutions (i.e., dextran 70 at 32% solids) has shown adverse reactions and little or no reduction of post-operative pelvic adhesions.

In addition, an oxidized cellulose fabric barrier (sold under the trade designation TC-7 by Johnson and Johnson Products, Inc., New Brunswick, N.J.), which is resorbable subsequent to utilization, has been used in the prior art as a treatment to prevent adhesions to the peritoneum by preventing abutting injured organ surfaces from making contact therewith. Chondroitin sulphate solutions have also been proposed for intraperitoneal use in the prevention of adhesions in rabbits. Each of these proposed methods of avoiding post operative adhesions have disadvantages which are overcome by the method of the present invention.

The mechanism of action of all of these treatments is proposed to be the result of the persistent separation of adjacent surgically injured surfaces thus permitting healing to occur without the formation of fibrinous bands between abutting surfaces which are characterized as adhesions. For instance, upon injury to the peritoneum there results an outpouring of a serosanguinous exudate which is of a proteinaceous nature. This fluid subsequently coagulates, producing fibrinous bands between abutting surfaces that become subsequently organized by fibroblast proliferation to produce collagenous adhesions. This process is thought to be initiated and well advanced within the first three days subsequent to surgical injury.

The polyoxyalkylene block copolymers which are utilized in the compositions of the invention can be viscous liquids, pastes, or granular solids. Where the copolymers are pastes, they can be used alone or in admixture with an optional humectant or low molecular weight polyoxyalkylene block copolymer having a molecular weight of less than 5000. Mixtures of granular block copolymers with at least one of said low molecular weight block copolymers or said viscous liquid block copolymers are also useful. A physiologically acceptable non-aqueous carrier or water can also be optionally added. Preferably, the copolymers, which are viscous liquids, are used in combination with water as a carrier or a non-aqueous carrier.

When the compositions of the invention are used in combination with water as a carrier, preferably the aqueous solutions have a block copolymer concentration which provides a free flowing liquid at ambient temperatures which gels upon contact with living mammalian tissue. Generally, the copolymers which are useful are selected from those defined above in formula I. Generally, the copolymer is selected from those copolymers which contain at least about 60% by weight, preferably at least about 70%, by weight and most preferably at least about 80% by weight of the residue of ethylene oxide (polyoxyethylene moiety). Generally, said copolymers have a total average molecular weight of at least about 5000, and form a gel at mammalian body temperature, when in an aqueous solution generally at a concentration of about 10 to about 40%, preferably about 15 to about 30% by weight and most preferably about 18% to about 25% by weight.

The proportion of carrier used is about 60% to about 90%, by weight preferably about 70% to about 85%, by weight and most preferably about 75% to about 82% by weight, based upon the total weight of the composition of the invention. Useful polyoxyalkylene block copolymers which will form gels in such aqueous solutions can be prepared using a hydrophobe base (such as A in Formulas I and II) derived from propylene oxide, butylene oxide, or mixtures thereof. These block copolymers and representative methods of preparation are further generally described in U.S. Pat. Nos. 2,677,700; 2,674,619; and U.S. Pat. No. 2,979,528, incorporated herein by reference.

Generally, the polyoxybutylene-based block copolymers useful in the compositions of the invention are prepared by first condensing 1,2 butylene oxide with a water soluble organic compound initiator containing 1 to about 6 carbon atoms such as 1,4 butylene glycol or propylene glycol and at least 2 reactive hydrogen atoms to prepare a polyoxyalkylene polymer hydrophobe of at least about 500, preferably at least about 1000, most preferably at least about 150 average molecular weight. Subsequently, the hydrophobe is capped with an ethylene oxide residue. Specific methods for preparing these compounds are described in U.S. Pat. No. 2,828,345 and British Patent No. 722,746, both of which are hereby incorporated by reference.

Useful polyoxybutylene based block copolymers conform to the following generic formula:

$$HO(C_2H_4O)_b(C_4H_8O)_a(C_2H_4O)_bH \qquad (III)$$

wherein a is an integer such that the hydrophobe base represented by $(C_4H_8O)$ has a molecular weight of at least about 500, preferably at least about 1000 and most preferably at least about 3000, as determined by hydroxyl number, the polyoxyethylene chain constituting at least 60%, preferably at least 70% by weight of the copolymer, and the copolymer having a total average molecular weight of at least 5000, preferably at least about 10,000, and most preferably at least about 15,000.

The copolymer is characterized in that all the hydrophobic oxybutylene groups are present in chains bonded to an organic radical at the former site of a reactive hydrogen atom thereby constituting a polyoxybutylene base copolymer. The hydrophilic oxyethylene grops are used to cap the polyoxybutylene base polymer.

Polyoxyethylene-polyoxypropylene block copolymers which can be used to form aqueous gels can be represented by the following formula:

$$HO(C_2H_4O)_b(C_3H_6O)_a(C_2H_4O)_bH \qquad (IV)$$

wherein a is an integer such that the hydrophobe base represented by (C₃H₆O) has a molecular weight of at least about 900, preferably at least about 2500, most preferably at least about 4000 average molecular weight, as determined by hydroxyl number; the polyoxyethylene chain constituting at least 60%, preferably at least 70% by weight of the copolymer, and the copolymer having a total average molecular weight of at least about 5000, preferably at least about 10,000, and most preferably at least about 15,000.

Polyoxyethylene-polyoxypropylene block copolymer adducts of ethylene diamine which can be used may be represented by the following formula:

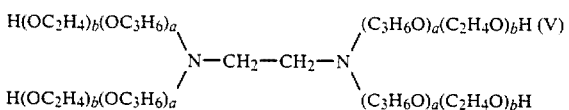

wherein a and b are integers such that the copolymer may have (1) a hydrophobe base molecular weight of at least about 2000, preferably at least about 3000, and most preferably at least about 4500, (2) a hydrophile content of at least 60%, preferably at least 70% by weight, and (3) a total average molecular weight of at least about 5000, preferably at least about 10,000, and most preferably at least about 15,000.

The hydrophobe base of the copolymer of formula V is prepared by adding propylene oxide for reaction at the site of the four reactive hydrogen atoms on the amine groups of ethylene diamine. An ethylene oxide residue is used to cap the hydrophobe base. These hydrophile polyoxyethylene groups are controlled so as to constitute at least 60%, preferably at least 70% by weight, and most preferably at least about 80% by weight of the copolymer.

The procedure used to prepare aqueous solutions which form gels of the polyoxyalkylene block copolymers is well known. Either a hot or cold process for forming the solutions can be used. A cold technique involves the steps of dissolving the polyoxyalkylene block copolymer at a temperature of about 5° to about 10° C. in water. When solution is complete the system is brought to room temperature whereupon it forms a gel. If the hot process of forming the gel is used the polymer is added to water heated to a temperature of about 75° C. to about 85° C. with slow stirring until a clear homogeneous solution is obtained. Upon cooling to room temperature, a clear gel is formed. Block copolymer gels containing polyoxybutylene hydrophobes must be prepared by the above hot process, since these will not liquify at low temperatures.

As used herein, the term "gel" is defined as a solid or semisolid colloid containing a certain quantity of water. The colloidal solution with water is often called a "hydrosol".

The organic compound initiator which is utilized in the process for the preparation of the polyoxyalkylene block copolymers generally is water or an organic compound and can contain a plurality of reactive hydrogen atoms. Preferably, Y in formulas I and II above is defined as derived from a water soluble organic compound having 1 to about 6 carbon atoms and containing x reactive hydrogen atoms where x has a value of at least 2. Falling within the scope of the compounds from which Y is derived are water soluble organic compounds such as propylene glycol, glycerin, pentaerythritol, trimethylolpropane, ethylene diamine, and mixtures thereof and the like.

The oxypropylene chains can optionally contain small amounts of at least one of oxyethylene or oxybutylene groups. Oxyethylene chains can optionally contain small amounts of at least one of oxypropylene or oxybutylene groups. Oxybutylene chains can optionally contain small amounts of at least one of ethylene or oxypropylene groups. The physical form of the polyoxyalkylene block copolymers can be a viscous liquid, a paste, or a solid granular material depending upon the molecular weight of the polymer. Useful polyoxyalkylene block copolymers generally have a total average molecular weight of about 5000 to about 50,000, preferably about 5,000 to about 35,000 and most preferably about 10,000 to about 25,000.

Preferably the polyoxyalkylene block copolymer is applied to surgically injured tissue as an aqueous solution which upon contact with living mammalian tissue forms a firm, adherent gel. Where an polyoxyalkylene block copolymer is a viscous liquid or paste, these compositions can be applied without dilution to areas of surgical injury in the abdominal or thoracic cavities. Where the block copolymers have the physical form of a paste or granular solid, it may be necessary or desirable to incorporate therewith either a low molecular weight liquid block copolymer, as defined herein, and/or a carrier liquid (solvent or a diluent).

The carrier solvent or diluent must be selected so as to be physiologically acceptable. Water, glycerine, and sorbitol are acceptable as solvents for the block copolymers. Other possibly acceptable solvents for the block copolymers are ethanol, isopropanol, n-butyl alcohol, tertiary butyl alcohol, cyclohexanone, hexylene glycol (2 methyl-2,4-pentanediol), butoxyethoxypropanol, butyl cellosolve®, butyl carbitol®, tetrahydrofuran, polyethylene glycols (liquid grades), polypropylene glycols having a molecular weight of less than 800, certain ketones, and propylene glycol. Generally, the block copolymers are insoluble in glycerol and mineral oil but these materials can be utilized as diluents, alone or in mixtures with the above solvents provided such mixtures are acceptable physiologically for application to injured tissue. Not all the above listed solvents for the block copolymers can be utilized in this invention since some of these may not be physiologically acceptable for application to an injured tissue or otherwise.

The following examples illustrate the various aspects of the invention but are not intended to limit its scope. Where not otherwise specified throughout this specification and claims, temperatures are given in degrees centigrade, and parts, percentages, and proportions are by weight.

EXAMPLE 1

An aqueous solution was made of a polyoxyethylene-polyoxypropylene block copolymer having the structure generically shown as formula IV and having a polyoxypropylene hydrophobe base average molecular weight of about 4000, a total average molecular weight of about 11,500, and containing oxyethylene groups in the amount of about 70% by weight of the total weight of copolymer. This copolymer is sold under the trademark PLURONIC® F-127 by the BASF Corporation, Parsippany, N.J. A solution was made by dissolving said polymer in cold (4° C.) distilled water to give a concentration of 30% by weight in accordance with the cold process described above for forming aqueous solutions. More specific solution procedures are described in "Artificial Skin I Preparation and Properties of Pluronic F-127 Gels for Treatment of Burns", *J. Biomed. Mater. Res.* 6, 527, 1972, incorporated herein by reference. The block copolymer has the formula:

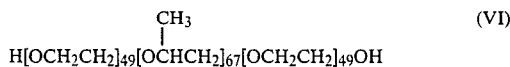

(VI)

This solution is a liquid at 4° C. and forms a gel which is adherent to living tissue upon contact. This solution was applied at 4° C. in the following experiments.

EXAMPLES 2-23

The following test procedure was utilized in order to determine the effect of the solution of Example 1 on surgically injured rats. Twenty-two female Sprague-Dawley rats having a 300-400 gram body weight were anesthetized with pentabarbital sodium (30 milligrams per kilogram of body weight) by application intraperitoneally through the left lumbar region of the ventral abdominal wall. The abdomen was thereafter opened by a 5 centimeter midline vertical incision subsequent to cleansing of the abdominal surface with providone-iodine solution and removing hair by shaving. A one centimeter segment of each uterine horn was stipped of serosa and an opposing one square centimeter of parietal peritoneum was excised, including the underlying muscle layer. Hemostasis was not attained.

Subsequently, the block copolymer solution of Example 1 was applied at a temperature of 4° C. to both the surgically injured area of the uterine horn and the parietal peritoneum surgical injury but only on one side of the abdomen. After the first application had formed a gel, a second layer of block copolymer solution was applied. Approximately 0.5 to 1.5 cubic centimeters of the block copolymer solution was applied depending upon the amount necessary to adequately cover (on one side of the abdomen) both the surgically injured one centimeter segment of the uterine horn and the surgically injured one square centimeter area of parietal peritoneal tissue.

The remaining side of the abdomen which was surgically injured in the same manner was left untreated. The portion of the uterine horn which was stripped of serosa was then attached within 0.5 centimeter of the surgical injury to the peritoneal parietal area by a single 3-0 VICRYL ligature suture. This was done to insure that the injured surface of the uterine horn remained in close proximity to the surgical injury of the parietal area of the peritoneum until re-peritonealization had occurred. The abdominal wall was closed with a single layer of interrupted 0-0 VICRYL suture and 21 days later each animal was sacrificed and the abdomen was examined for the presence of adhesions.

The following grading system was used to evaluate the results obtained:
0 = no adhesion observed.
1 = adhesions on 25% of the surgically injured area.
2 = adhesions on 50% of the surgically injured area.
3 = adhesions on 100% of the surgically injured area.

The tenacity of the adhesion which formed was evaluated according to the following grading system.
0.0 = no resistance to separation.
0.5 = moderate force of separation required to rupture the adhesion.
1.0 = strong force or cutting necessary for separation.

A rating for the results obtained was obtained by adding the results in each of the grading systems. Results therefore would range from 0.0 to 4.0 for each surgically injured area evaluated. The data were analyzed by a rank sum test and also by analysis of variance.

Since the bilaterally surgically injured areas of each rat were treated with block copolymer solution only unilaterally, each rat served as its own control. Twenty of the 22 rats used in the evaluation survived a 21 day period prior to sacrifice. Two animals died from failure to adequately close the abdominal incision to seal the peritoneal cavity and its contents.

Nineteen of the 20 surviving animals developed adhesions on the untreated control side of the abdomen. The combined score for the untreated control, including area and tenacity of the adhesions, averaged 3.2. On the block copolymer solution treated side of the abdomen, in 8 of the 20 surviving rats, some degree of adhesion was noted. The combined score, for the block copolymer treated areas including area and tenacity of adhesions in these 8 rats averaged only 1.63. These results taken with the results for the block copolymer treated side of the remaining 12 rats having no adhesions provided a combined average score of only 0.7. This difference is considered statistically significant at the p less than 0.005 level.

EXAMPLES 24-46

The procedure of Examples 2-23 is repeated utilizing a 20% by weight aqueous solution of a polyoxybutylene-based block copolymer having the structure generically shown as formula III and having a polyoxybutylene hydrophobe base having an average molecular weight of 3000 and a total average molecular weight of 10,000. Substantially similar results are obtained following the test procedure of Examples 2-23.

EXAMPLES 47-69

Utilizing a 30% by weight aqueous solution of a polyoxyethylene-polyoxypropylene block copolymer having the structure generically shown in formula I and having a polyoxypropylene hydrophobe base molecular weight of 2000, a polyoxyethylene content of 70% by weight, and a total average molecular weight of 5000, the test procedure of Examples 2-23 is repeated to obtain substantially the same results.

EXAMPLES 70-92

The procedure of Examples 2-23 is repeated using a 30% by weight aqueous solution of a polyoxyethylene-polyoxypropylene block copolymer adduct of ethylene diamine having a hydrophobe molecular weight of 1500 and a total average molecular weight of 2500, said copolymer having a hydrophile content of 60% by weight and a total average molecular weight of 5500. Substantially similar results are obtained.

While this invention has been described with reference to certain specific requirements embodiments, it will be recognized by those skilled in the art that many variations are possible without departing from the scope and spirit of the invention, and it will be understood that it is intended to cover all changes and modifications of the invention, disclosed herein for the purposes of illustration, which do not constitute departures from the spirit and scope of the invention.

The embodiments of the invention in which an exclusive property or privilege is claimed are defined as follows:

1. A process for reducing post-surgical adhesion formation/reformation following surgical injury to organs situated in the mammalian peritoneal or pleural cavity, comprising separating said organs from adjacent tissue with an effective amount of a composition comprising: a polyoxyalkylene block copolymer of the formula $$Y[(A)_n-E-H]_x \qquad (I)$$

wherein A is an oxyalkylene moiety having an oxygen/carbon atom ratio of less than 0.5, x is at least 1, Y is derived from water or an organic compound containing x reactive hydrogen atoms, E is a polyoxyethylene moiety, n has a value such that the average molecular weight of A is at least about 500 to about 900, as determined by the hydroxyl number of an intermediate, $$Y[(A)_n-H]_x \qquad (II)$$

and the total average molecular weight of the copolymer is at least 5000.

2. The process of claim 1 wherein Y in said formulas I and II is a water soluble organic compound having 1–6 carbon atoms, and said copolymer is selected from the group consisting of a polyoxyethylene-polyoxybutylene block copolymer, a polyoxyethylene-polyoxypropylene block copolymer and mixtures thereof, wherein the polyoxyethylene moiety constitutes at least 70% by weight of the polymer and wherein said composition includes a physiologically acceptable carrier liquid.

3. The process of claim 2 wherein said copolymer is selected from block copolymers which form aqueous gels at a concentration of about 10–40% by weight of the total weight of said composition.

4. The process of claim 3 wherein said Y is derived from a compound selected from the group consisting of propylene glycol, butylene glycol, glycerin, pentaerythritol, trimethylolpropane, ethylenediamine, and mixtures thereof, and said carrier liquid is water.

5. The process of claim 4 wherein Y is derived from propylene glycol, A is the residue of propylene oxide, and the intermediate of Formula II has an average molecular weight of at least about 900.

6. The process of claim 4 wherein Y is derived from butylene glycol, A is the residue of butylene oxide, and the intermediate of Formula II has an average molecular weight of at least about 500.

7. The process of claim 5 or claim 6 wherein said polymer has the formula $$HO(C_2H_4O)_b(C_4H_8O)_a(C_2H_4O)_bH \qquad (III)$$

wherein in III, a is an integer such that the hydrophobe base represented by $(C_4H_8O)$ has a molecular weight of at least 1000, as determined by hydroxyl number, the polyoxyethylene chain constitutes at least about 60% by weight of the copolymer, and the copolymer has a total average molecular weight of at least 5,000, or $$HO(C_2H_4O)_b(C_3H_4O)_a(C_2H_4O)_bH \qquad (IV)$$

wherein in IV, a is an integer such that the hydrophobe base represented by $(C_3H_6O)$ has a molecular weight of at least about 1500 average molecular weight, as determined by hydroxyl number, the polyoxyethylene chain constitutes at least about 60% by weight of the copolymer, and the copolymer has a total average molecular weight of at least 5,000 or

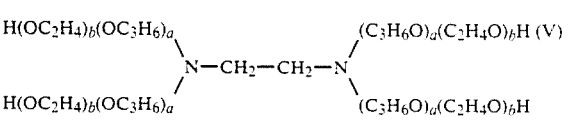

wherein in V a and b are integers such that the copolymer has a hydrophobe molecular weight of at least about 2000, a hydrophile content of at least about 60%, and a total average molecular weight of at least about 5,000.

8. The process of claim 7 wherein said copolymer is $$H[OCH_2CH_2]_{49}[OCHCH_2]_{67}[OCH_2CH_2]_{49}OH \qquad (VI)$$
$$\text{with } CH_3 \text{ substituent}$$

9. The process of claim 8 wherein said copolymer is present is a concentration of about 15% to about 30% by weight of the total weight of said composition and said composition is a liquid at ambient temperature and forms a gel upon contact with said mammalian tissue.

10. The process of claim 9 wherein said composition contains at least one of a humectant, a bactericide, a bacteriostatic agent, an agent to prevent leucocyte migration into an area of surgical injury, and a fibrinolytic agent.

* * * * *